United States Patent [19]
Linker, Jr.

[11] Patent Number: 5,113,916
[45] Date of Patent: May 19, 1992

[54] LEAD STRAIGHTENING METHOD AND APPARATUS

[75] Inventor: Frank V. Linker, Jr., Broomall, Pa.
[73] Assignee: American Tech Manufacturing Corporation, Glenolden, Pa.
[21] Appl. No.: 565,438
[22] Filed: Aug. 9, 1990
[51] Int. Cl.⁵ .............................................. B21F 1/02
[52] U.S. Cl. .................................................. 140/147
[58] Field of Search ............................... 140/140, 147

[56] References Cited

U.S. PATENT DOCUMENTS 3,687,172  8/1972  Suver-Kropp ....................... 140/147
4,481,984 11/1984  Linker ................................. 140/147

FOREIGN PATENT DOCUMENTS 0162519  6/1989  Japan ................................... 140/147

*Primary Examiner*—Lowell A. Larson
*Assistant Examiner*—Michael J. McKeon
*Attorney, Agent, or Firm*—Eugene Renz

[57] ABSTRACT

Apparatus and method for aligning the leads of electronic devices having a body portion and plurality of leads extending from the body portion having pads at the free terminal ends comprising means for positioning the electronic device at a lead straightening station. A pair of lead straightening heads comprised of a plurality of fingers engages between the leads on opposite sides of the electronic device. The lead straightening heads are actuated relative to the electronic device through a straightening cycle including a first phase where the fingers engage between leads of the electronic device while in a floating condition and a second phase after the electronic device is clamped in place on a support surface to pivot the leads on either side of a plane extending transversely to the body portion and thereby align each of the leads relative to this plane. Coplanarity means is provided for positioning the pads of the leads so that they all lie in a common plane.

21 Claims, 10 Drawing Sheets

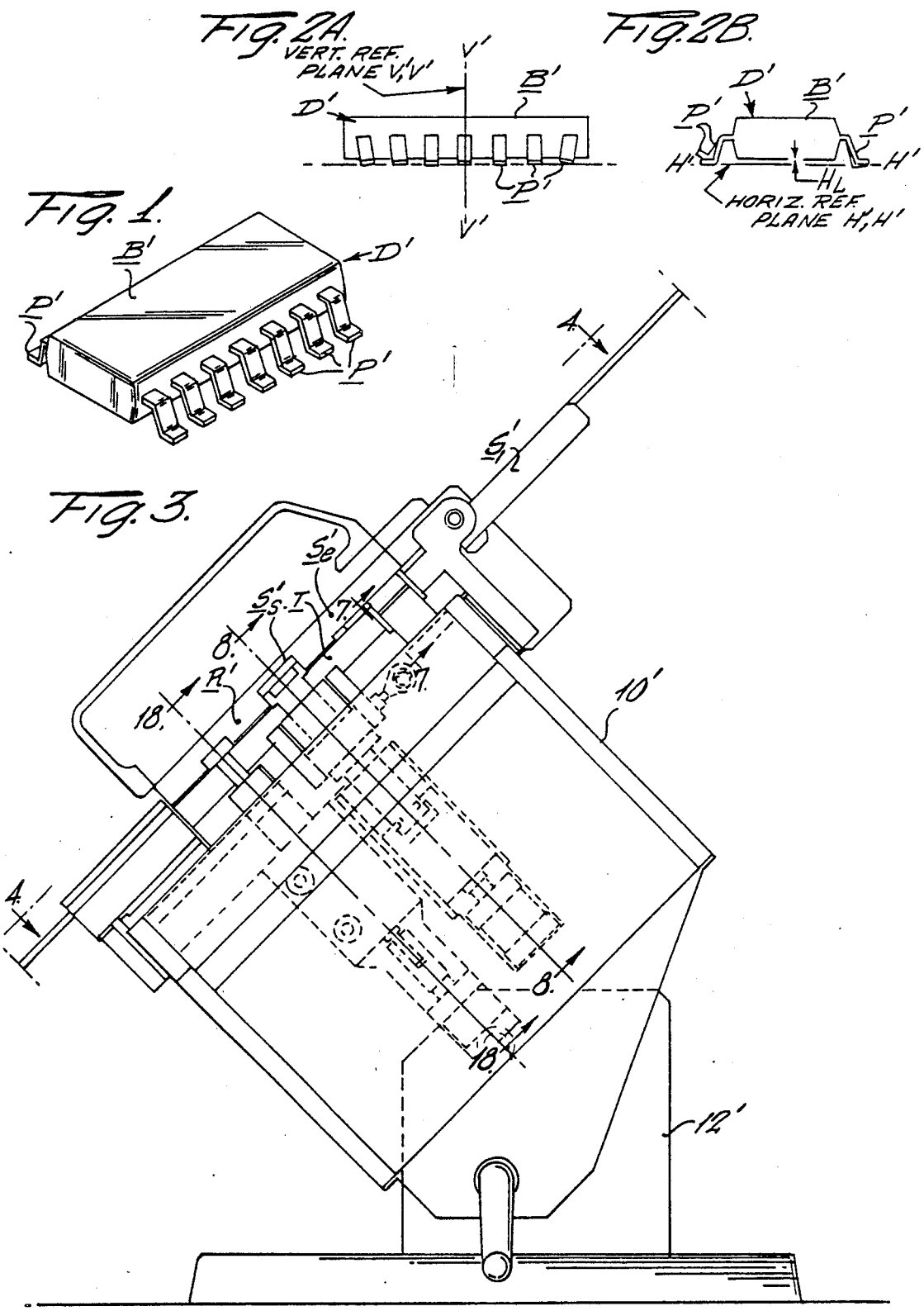

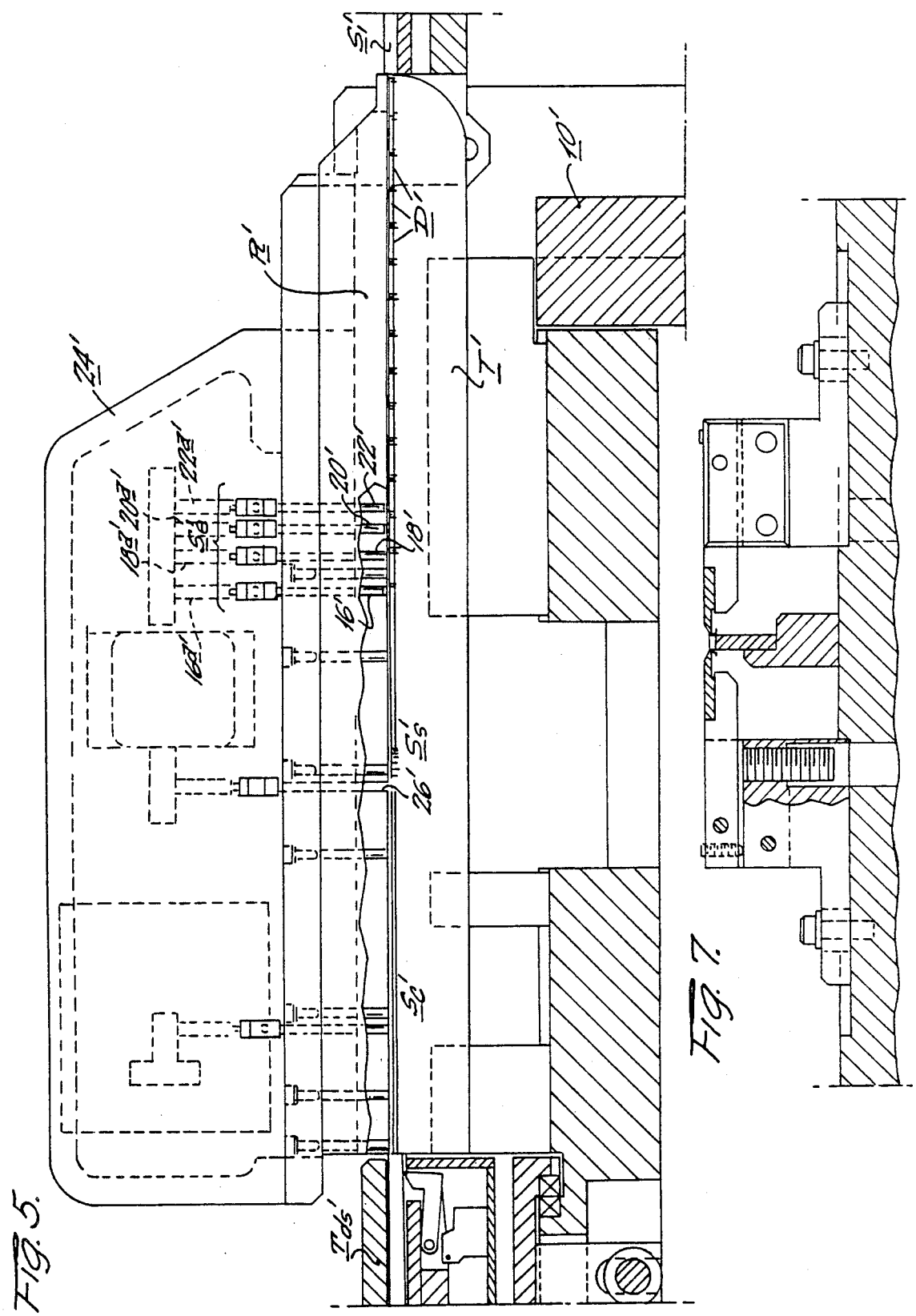

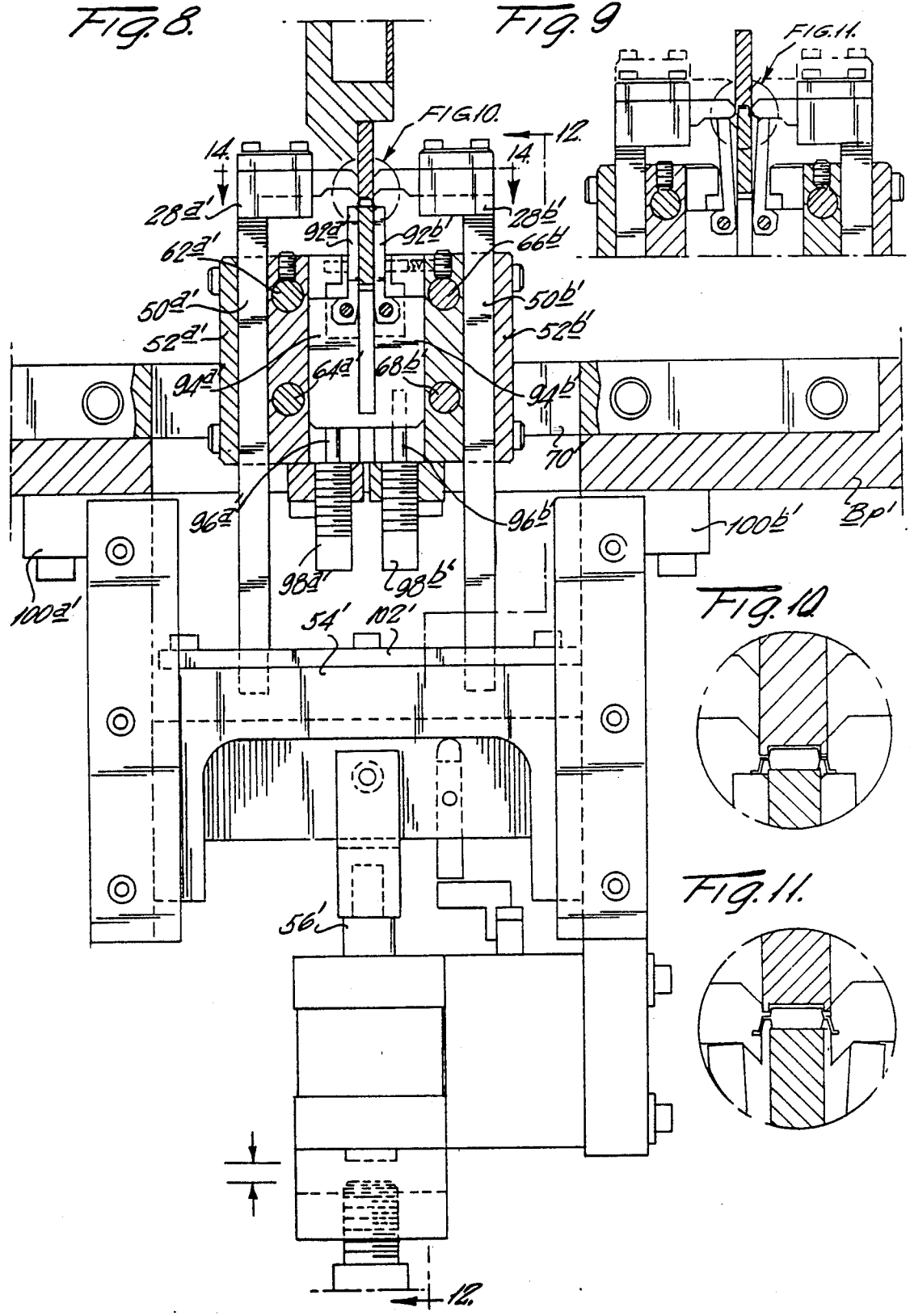

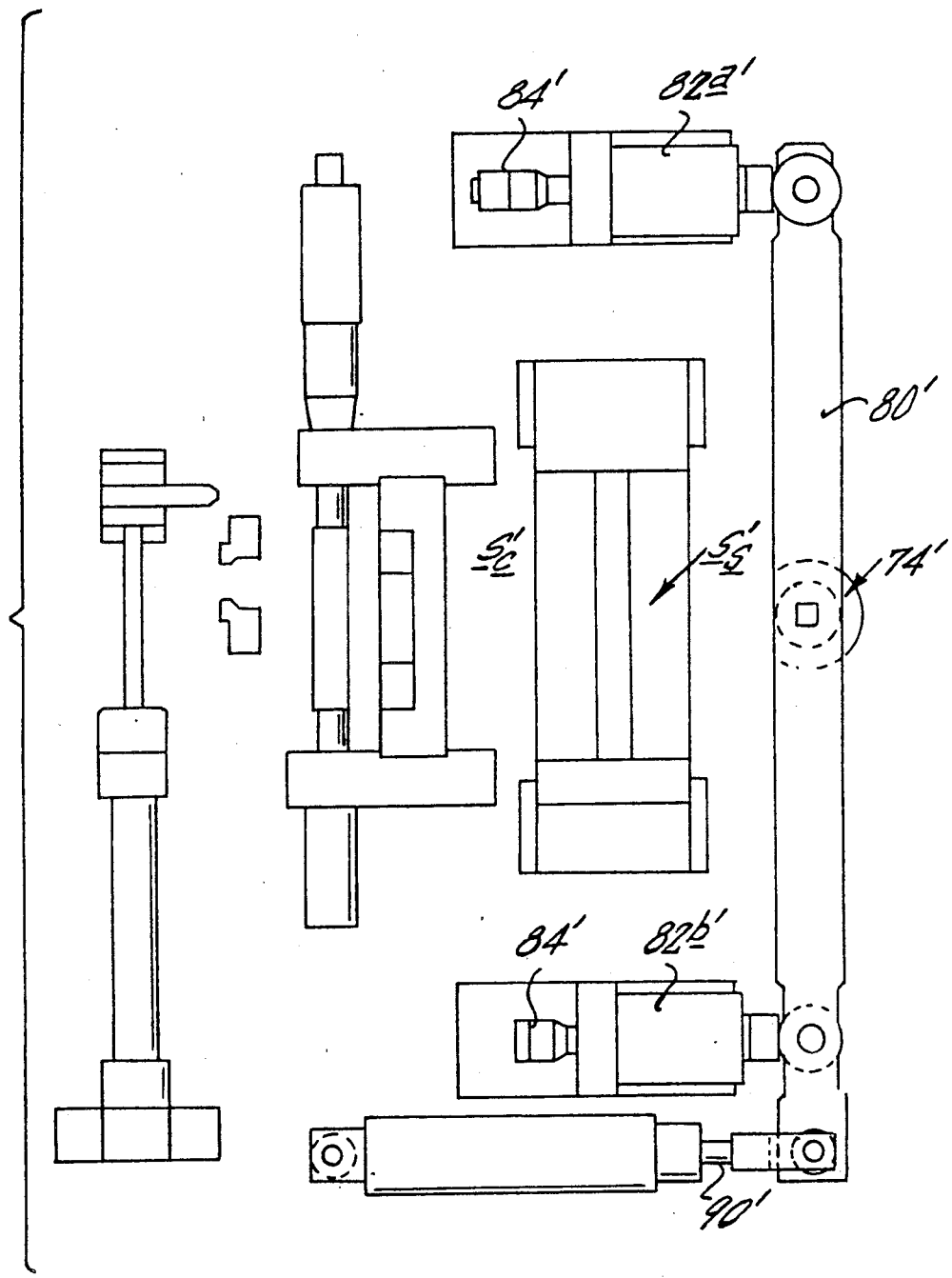

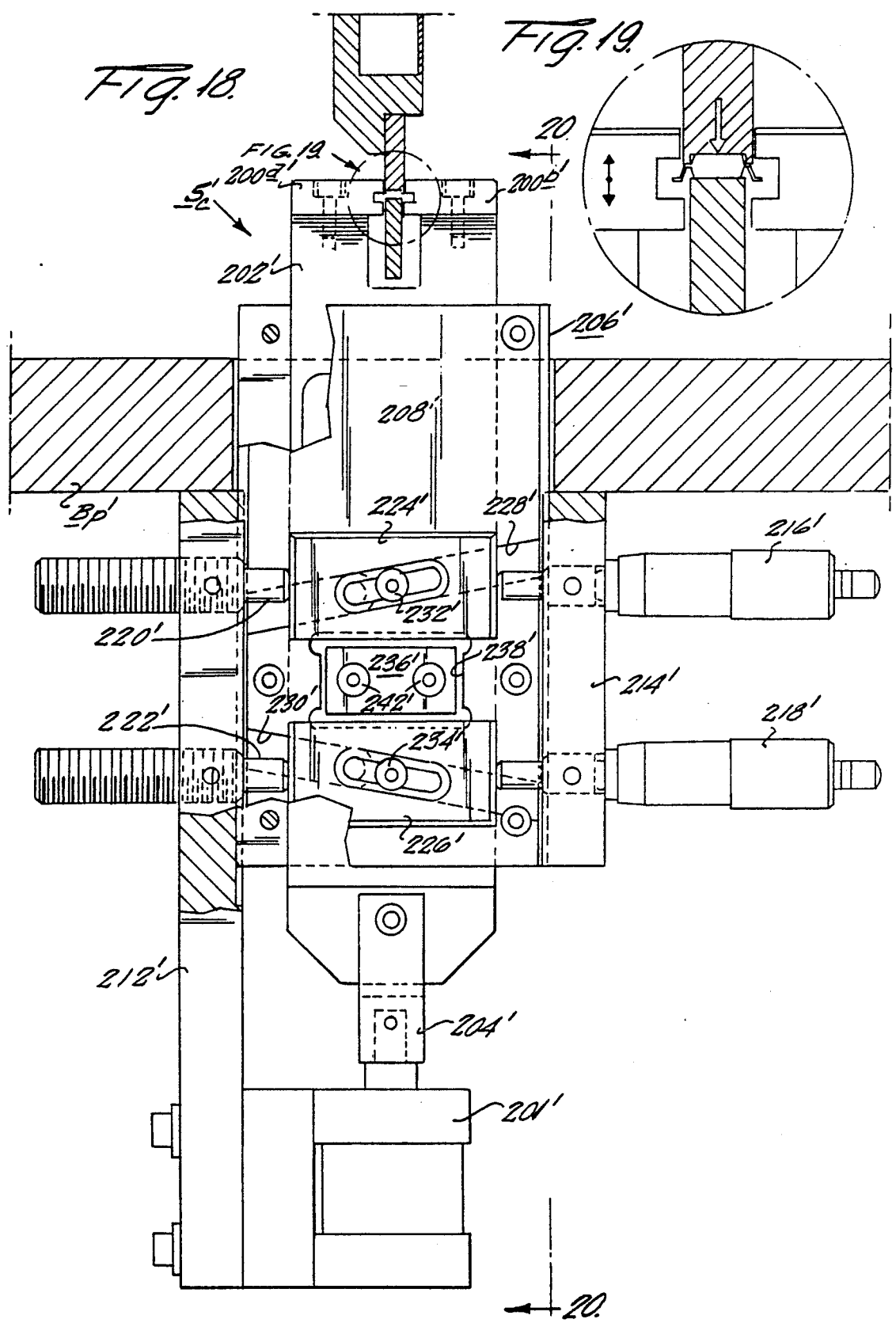

LEAD STRAIGHTENING METHOD AND APPARATUS

FIELD OF THE INVENTION

The present invention relates generally to improvements in apparatus and methods for straightening electronic components of the type commonly referred to as DIP devices. These devices are used as semi-conductors or resistors in integrated circuit boards or the like. More specifically, the apparatus and the method of the present invention are designed for straightening a relatively new type of DIP device, a so-called "gull-winged" DIP device.

BACKGROUND OF THE INVENTION

Apparatus and system for straightening DIP devices are not new per se. There are several patents owned by the common assignee of the present application showing apparatus and system for straightening DIP devices which have a generally rectangular body portion and a series of a fingers or leads projecting from opposite side edges of the body portion which are generally elongated straight fingers.

| Inventor | Title | U.S. Pat. No. | Issued |
| --- | --- | --- | --- |
| Linker | ELECTRONIC COMPONENT LEAD STRAIGHTENING DEVICE & METHOD | 4,481,984 | 11/13/84 |
| Linker | HIGH SPEED ELECTRICAL COMPONENT LEAD FORMING APPARATUS & METHOD | 4,787,426 | 11/29/88 |

In these apparatus, the DIPs are usually fed by gravity along an elongated trackway through various stations including a lead straightening station where the fingers of combs moving transversely to the trackway engage between the fingers and in this manner align the leads in relation to one another. These prior apparatus have been found to be effective for the purposes intended. However, the "gull-winged" DIP device because of the complex shape of the leads which are generally Z-shaped configuration present different problems in the straightening or aligning process. Furthermore, in the "gull-winged" DIP devices, it is essential that the pads of the leads lie in a common plane for proper assembly to the printed circuit board. In other words, there needs to be coplanarity of the pads before a DIP device is suitable for assembly.

SUMMARY OF THE INVENTION

With the foregoing in mind, it is an object of the present invention to provide a new and improved apparatus and system for straightening and effecting coplanarity of the leads of "gull-winged" DIP devices characterized by novel features of construction and arrangement to precisely align the leads and work them in a manner to achieve coplanarity without inflicting damage on the leads during the processing cycle. To this end, in accordance with the present invention, the DIP devices which are usually housed in elongated tubes in end to end array are fed through the machine on an elongated trackway by gravity. DIPs discharge to the trackway are retained by an elongated adjustable upper guide and clamping rail spaced a predetermined distance above the trackway to allow free movement of the DIPs through the apparatus.

An escapement system singulates the DIPs so that they move in an orderly fashion one at a time through various stations downstream of the escapement station. The escapement system has a novel arrangement of DIP retaining elements which are selectively adjustable to accommodate DIPs of different lengths and still provide the desired one at a time passage through the apparatus.

The DIPs entering a straightening station downstream of the escapement system are aligned so that straightening jaws comprised of a plurality of blades having straightening fingers will engage in the spaces between the leads. At the straightening station, the blades engage between the leads on both sides while the DIP device is in a "floating" condition on the trackway. In this position, the DIP is clamped to the trackway and thereafter the jaws are oscillated to move each of the pins back and forth relative to a vertical plane in a predetermined cycle to effect the desired straightening action. It has been found that the Z-shaped gull winged leads tend to be deformed or bend at the juncture of the lead to the body portion rather than being deformed along their length. Thus, the novel straightening action described is effective to properly align the leads relative to a vertical plane.

After the jaws are cycled, the straightened DIP is released and moves to a coplanarity station downstream of the straightening station. Here the DIP is retained and secured in a fixed position and the pads of the leads on both sides are located in the bite or cavity of a pair of coplanarity jaws. With the DIP device clamped in place, the jaws are cycled in an up and down plane relative to the trackway to pivot the leads about the shoulder at the juncture of the lead and body portion in a direction generally transverse to that described above in connection with the lead straightening cycle. At the straightening and coplanarity stations, the action described effectively removes or eliminates the elastic memory of the material so that the leads once properly oriented will remain in that position in the pattern and spacing desired for proper assembly to a PCB.

BRIEF DESCRIPTION OF THE DRAWINGS

These and other objects of the present invention and the various features and details of the operation and construction thereof are hereinafter more fully set forth with reference to the accompanying drawings, wherein:

FIG. 1 is a perspective view of a typical gull winged DIP device;

FIG. 2a is a side elevational view of a gull winged DIP device shown in FIG. 1 but showing some leads bent with respect to a normal vertical reference plane V—V;

FIG. 2b is a front elevational view of the gull winged DIP device shown in FIG. 1 showing some of the leads bent above and below a horizontal reference plane;

FIG. 3 is a side elevational view of the pin straightening and coplanarity adjusting apparatus in accordance with the present invention for correcting the misalignment of the DIP device leads in both the vertical and horizontal planes;

FIG. 5 is an enlarged fragmentary sectional elevational view taken on lines 5—5 of FIG. 4 showing details of the DIP support rail and its cooperating guide and clamping rail mechanism extending from the DIP input station to a DIP discharge station;

FIG. 7 is a fragmentary sectional elevational view taken transversely through the apparatus along line 7—7 of FIG. 3 showing the emergency-job interrupt DIP hold down device adjacent the input station for holding the DIPS on the rail at the input station;

FIG. 8 is an enlarged fragmentary sectional elevational view taken along line 8—8 of FIG. 3 showing the pin straightening station;

FIG. 9 is a fragmentary sectional view of the pin straightening station showing the straightening heads in an operative mode or position;

FIGS. 10 and 11 are greatly enlarged fragmentary sectional views of the details contained within the circular dash lines in FIGS. 8 and 9 respectively;

FIG. 17 is a schematic bottom plan view taken on line 17—17 of FIG. 3 showing additional components and details of the oscillating mechanism;

FIG. 18 is an enlarged transverse sectional view taken on line 18—18 of FIG. 3 showing some of the details of the coplanarity adjusting station;

FIG. 19 is an enlarged fragmentary sectional view of the details contained within the dot and dash circle of FIG. 18 showing the coplanarity heads in a neutral or rest position, and the clamping head exerting a downward force clamping the DIP to the tracking;

DETAILED DESCRIPTION OF THE PREFERRED EMBODIMENT

The apparatus of the present invention is designed particularly for straightening the pins P of so-called gull winged DIP devices of the type illustrated in FIG. 1. These DIPS generally comprise an elongated generally rectangular body portion B made of a molded material such as a plastic and having embedded therein along opposing side edges a plurality of pins or leads P of generally Z shaped configuration. The lower portions of the Z shaped pins are commonly referred to as the pads Pp and for proper installation need to be precisely aligned in a common horizontal reference plane H—H. It is also important that the leads or pins P be aligned relative to a vertical plane V—V. These alignments are extremely important and critical to ensure proper installation to a PC board. It has been found that the pins or leads P are extremely delicate and that they tend to misalign during handling and shipment, particularly the leading and trailing pins P at opposite ends of the body portion B. The apparatus and method of the present invention are designed for straightening the pins P so that they are aligned relative to the vertical plane V—V and also to produce coplanarity or alignment of all the pads Pp in the horizontal plane H—H. Even though the method and apparatus of the present invention are particularly suited for these operations on so-called gull winged DIP devices, it is of course to be understood that the apparatus and method ma be employed for DIP devices of various sizes as well as performing other operations.

Figure 4:
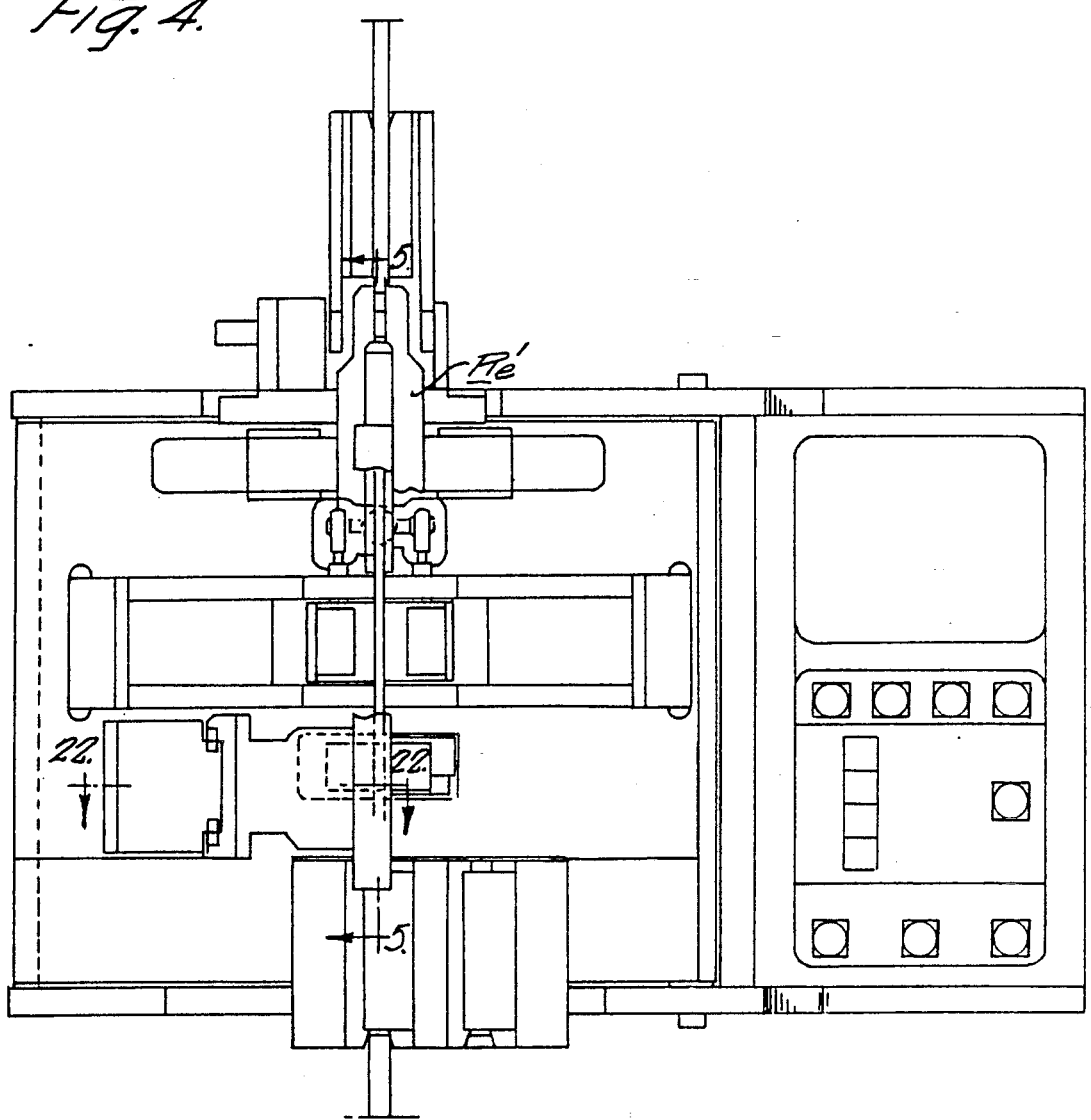
FIG. 4 is an auxiliary plan view of the pin straightening and coplanarity adjusting apparatus of the present invention taken on lines 4—4 of FIG. 1 showing additional details of the apparatus.

The novel DIP straightening and coplanarity mechanisms of the present invention will be described hereinafter in conjunction with the description of the overall apparatus. A general understanding of the basic structure and operation of the apparatus including the novel pin straightening and pin coplanarity mechanism may be gained by reference to several of the views which best show the basic components of the apparatus and the operation thereof, such as FIGS. 3 and 4.

Considering first, however, the basic components of the entire apparatus in terms of function, the apparatus shown in FIG. 3 comprises a main housing 10 pivotally mounted on a pedestal or base 12. The housing 10 is selectively adjustable relative to the base 12 to dispose the upper face 10a of the apparatus at a desired inclined angle, for example, from 35° to 55° so that DIPS can move through the various stations by gravity.

An elongated trackway T is mounted on the upper face 10a of the housing. A DIP loading station $S_L$ is located at the upper end of the trackway T having a pivotally mounted loading cartridge holder for supporting the tubes within which the DIPS are carried for processing. When the tube is aligned with the trackway T, the DIPS to be processed discharge from the loading station $S_L$ directly to the upper end of the trackway T, where as illustrated in FIG. 10, the DIPS straddle the trackway T so that their leads or pins P are disposed on either side thereof. The DIPS are retained on the trackway T by an elongated adjustable upper guide and clamping rail assembly $C_R$ which, in the operative position shown in FIG. 5, is spaced relative to the trackway T to allow free movement of the DIPS along the trackway T.

Figure 15:
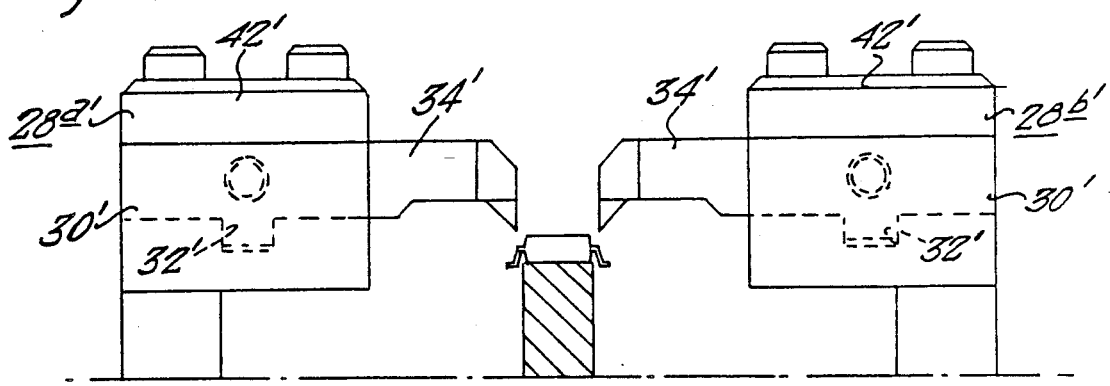
FIG. 15 is a fragmentary elevational view of the straightening heads shown in FIG. 14.

An escapement station $S_e$ is located downstream of the loading station $S_L$ the function is to permit discharge of one DIP device at a time through the various other stations downstream of the escapement station $S_e$. Single DIP devices discharged from the escapement station $S_e$ are moved by gravity to the pin straightening station $S_s$ where a DIP engages an index pin to properly position the DIP device relative to the pin straightening mechanism during a pin straightening cycle. The pin straightening station includes a pair of cooperating lead straightening heads comprised of a series of blades of the general profile shown in FIG. 15 which engage between the pins P while the DIP device is still in an unsecured or floating mode. At this point in the cycle, the DIP device is clamped to the trackway T by the guide and clamping rail assembly $C_R$. The pin straightening heads ar then oscillated to effect the straightening action and align the pins relative to the vertical plane V—V.

DIPS so straightened at the pin straightening station $S_s$ are then released and move along the trackway T to the coplanarity station $S_c$ located downstream of the pin straightening station $S_s$ (see FIGS. 5 and 18-21). As the DIP device enters this station, it engages another locating pin which positions the DIP between a pair of coplanarity jaws. The pins of the DIP device lie in the bite of a pair of the coplanarity jaws. In this position the DIP device is again clamped to the trackway T by the clamp and guide rail assembly $C_R$. The jaws are then cycled in a predetermined pattern to engage the pads of the DIP device first in a downward stroke bending all the pads of the DIP device below a selected horizontal reference plane H—H. Then the pads are driven upwards to the desired horizontal plane H—H and the coplanarity jaws are returned to a neutral position. It has been found that this cycling procedure results in coplanarity of all the pads $P_p$.

Upon completion of the coplanarity adjustment cycle, the positioning pin is retracted, the clamping guide rail $C_R$ is elevated so that the DIP device is now free to discharge by gravity to a discharge station $TD_S$ where the processed DIP devices are again accumulated in the elongated collection tubes.

A logic keyboard for operating the various mechanisms of the apparatus of the present invention in predetermined timed sequences is provided which is of relatively standard form. An example of a typical logic keyboard and circuitry for achieving the controlled operation described herein is shown in Linker Patent No. 4,686,637, entitled APPARATUS AND METHOD FOR LEAD INTEGRITY DETERMINATION FOR DIP DEVICES granted Aug. 11, 1987.

There are instances where it is necessary to access the trackway T while DIP devices are located in the escapement station $S_e$. For example, due to power failure or jamming, it may be necessary to remove the clamping and guide rail assembly $C_R$. Thus, the apparatus includes restraining elements in the form vanes $R_e$ located on either side of the trackway T which normally are spaced from the DIPs to allow free movement of the DIPs on the trackway by gravity, However, in the event of a power failure the vanes $R_e$ are released to a position to engage the DIP devices on the trackway and to retain them even when the guide and clamping rail assembly $C_R$ is displaced from its normal operating position and would no longer function to encapsulate DIPs on the trackway. A manually operable system is provided for removing the clamping and guide rail assembly $C_R$ if necessary, in the event of a power failure or jamming for access to internal parts of the machine inaccessible when the clamp and guide rail $C_R$ is in the operative position. This manually operable system is also useful when initially setting up the apparatus, for a particular DIP device.

The apparatus includes a tube discharge station $T_{ds}$ at the lower end of the trackway to receive processed DIP devices.

Figure 6:
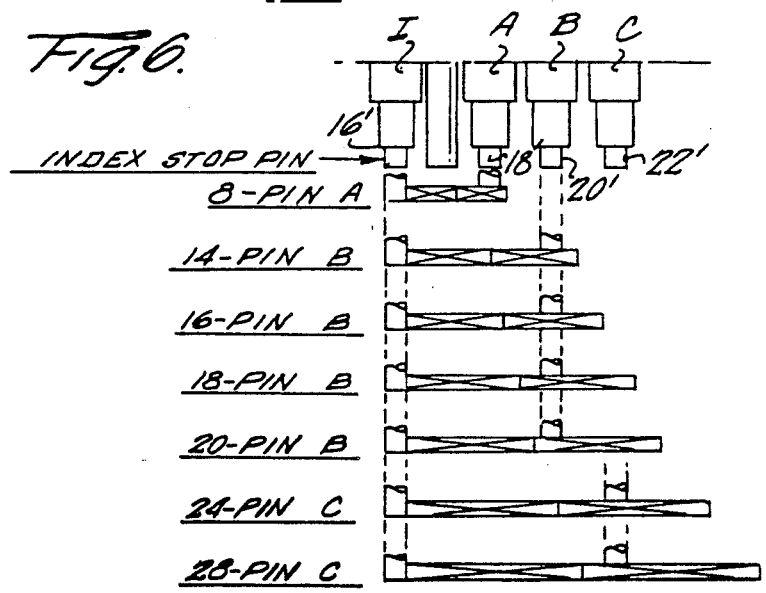
FIG. 6 is a schematic enlarged fragmentary side elevational view of the escapement zone, inset in the upper guide and clamping rail assembly, adjacent the input end of the trackway illustrating the indexing and timed release of DIP devices and schematically showing three escapement cylinders and the use of each particular one with respect to the size of the DIP device to be run, ranging in size from eight (8) to twenty-eight (28) pins

There are a number of photo-electric sensing cells $P_e$ located in the guide rail assembly which are aligned with the trackway T and track the path of DIP devices through the apparatus. These photo-electric sensing devices function in the overall logic circuit to trigger the desired mechanical function of the machine in the manner described herein. These sensors act in pairs, one to project a beam and the other to receive the beam in a conventional fashion. FIG. 6 schematically shows the functioning of the escapement mechanism for the different size DIP devices ranging from between eight (8) pin device to a twenty-eight (28) pin device.

Considering now more specifically the details and structural arrangement of the escapement station $S_e$, and with particular reference to FIGS. 5 and 6, there is provided a series of escapement pins 16, 18, 20 and 22 mounted in the clamping and upper guide rail housing 24 for reciprocating motion therein. The pins are mounted for reciprocating movement by spring biased air actuator assemblies 16a, 18a, 20a, and 22a. The lead pin 16 is an index pin for all DIP sizes and functions to retain the line of DIPS at the escapement station $S_e$ in the manner illustrated. The other three pins, 18, 20, and 22 are designated clamping pins and are selectively actuated in unison with the stop pin 16 depending on the size of the DIP device being run. For example, index pin 16 is only retracted to release a DIP device when one of the three remaining clamping pins is in an operative or clamping mode. This produces release of one DIP device at a time from the escapement station $S_e$ to the pin straightening station $S_s$.

Figure 14:
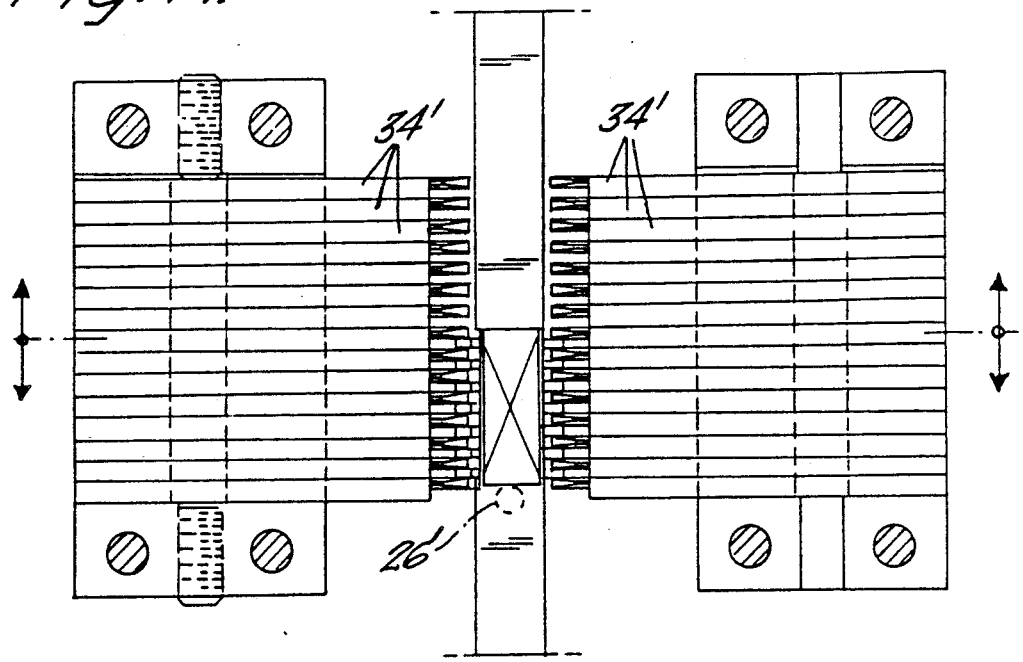
FIG. 14 is a fragmentary sectional plan view taken on line 14—14 of FIG. 8 showing the position of the straightening heads relative to a DIP device at the pin straightening station.

A single DIP device released from the escapement station $S_e$ moves down the trackway T until it engages a second indexing pin 26 at pin straightening station. The indexing pin 26 as best shown in FIGS. 5 and 14 is aligned with the straightening heads 28a and 28b so that it positions the front edge of a DIP device in the correct operative position for leafing inter-engagement of the blades 34 in the spaces between the DIP device pins P. The location of the indexing pin 26 need not be totally precise so long as it generally orients the DIP device so that each of the blades can engage in a space between the DIP device pins. The DIP device is in a floating condition on the trackway T in this part of the straightening cycle.

The pin straightening station $S_s$ comprises a pair of cooperating pin straightening heads 28a and 28b. Each head is of identical construction and comprises a U-shaped block 30 having an elongated key slot 32 in its base and a plurality of elongated straightening blades 34. The blades 34 comprise an elongated body 36 having a depending lug 38 which keys in the slot 32 in the housing to align the blades so that the straightening blades teeth 40 are aligned in the manner shown in FIG. 14. The blades are kept in a tight abutting side to side relation by means of set screws and opposing upright end portions of the block 28. The blades are anchored in the block by means of a cap 42. Even though the straightening heads comprise a plurality of discrete fingers which are keyed in place so that the finger tips align, the finger assembly may comprise a unitary integral element comprised of a plurality of finger tips of essentially the same configuration as those shown and described herein.

Means are provided for cycling the heads 28a, 28b in a predetermined sequence when a DIP device is located at the straightening station $S_s$ to effect straightening the leads or pins P relative to the vertical plane V—V. FIGS. 8 and 10 show the "home" position of the straightening heads. The heads 28a, 28b are moved downwardly initially in the straightening cycle to a point where the tips 40a of the blades 36 are located intermediate the pads and the shoulder of the pins of the leads as shown in FIG. 11. With the straightening heads in this position, the guide rail $C_R$ is actuated downwardly to clamp the DIP at the straightening station $S_s$ against the trackway T so that it is immovable. Thereafter, the heads 28a, 28b are oscillated in a horizontal plane parallel to the axis of the trackway T to bend each of the leads to either side of its true vertical alignment. It has been observed that this action allows for spring back and aligns each of the pins P in the vertical plane V—V in the desired parallel orientation of the pins as viewed from the side of a DIP device. In a typical DIP device the spacing between the pins P is 0.050 inches and the pins are approximately 0.014 inches wide. Thus in a typical cycle the pins are displaced about 0.003 inches from the vertical plane VV to either side.

Considering now more specifically the means for effecting cycling and actuation of the straightening heads 28a, 28b in the manner described above and with reference to FIG. 8, the head, are mounted on elongated slides 50a and 50b which are slidably engaged in slide retaining blocks 52a and 52b. The elongated slides 50a and 50b are connected at their lower ends with a cross head 54 (see FIG. 8) which in turn is connected to a piston-cylinder actuator 56. Accordingly cycling of the piston-cylinder actuator 56 effects reciprocating up and down movement of the cross head 54, the connected slides 52a and 52b, and the pin straightening heads 28a and 28b to cycle the heads from the home position shown in FIG. 10 to the straightening position shown in FIG. 11.

Figure 12:
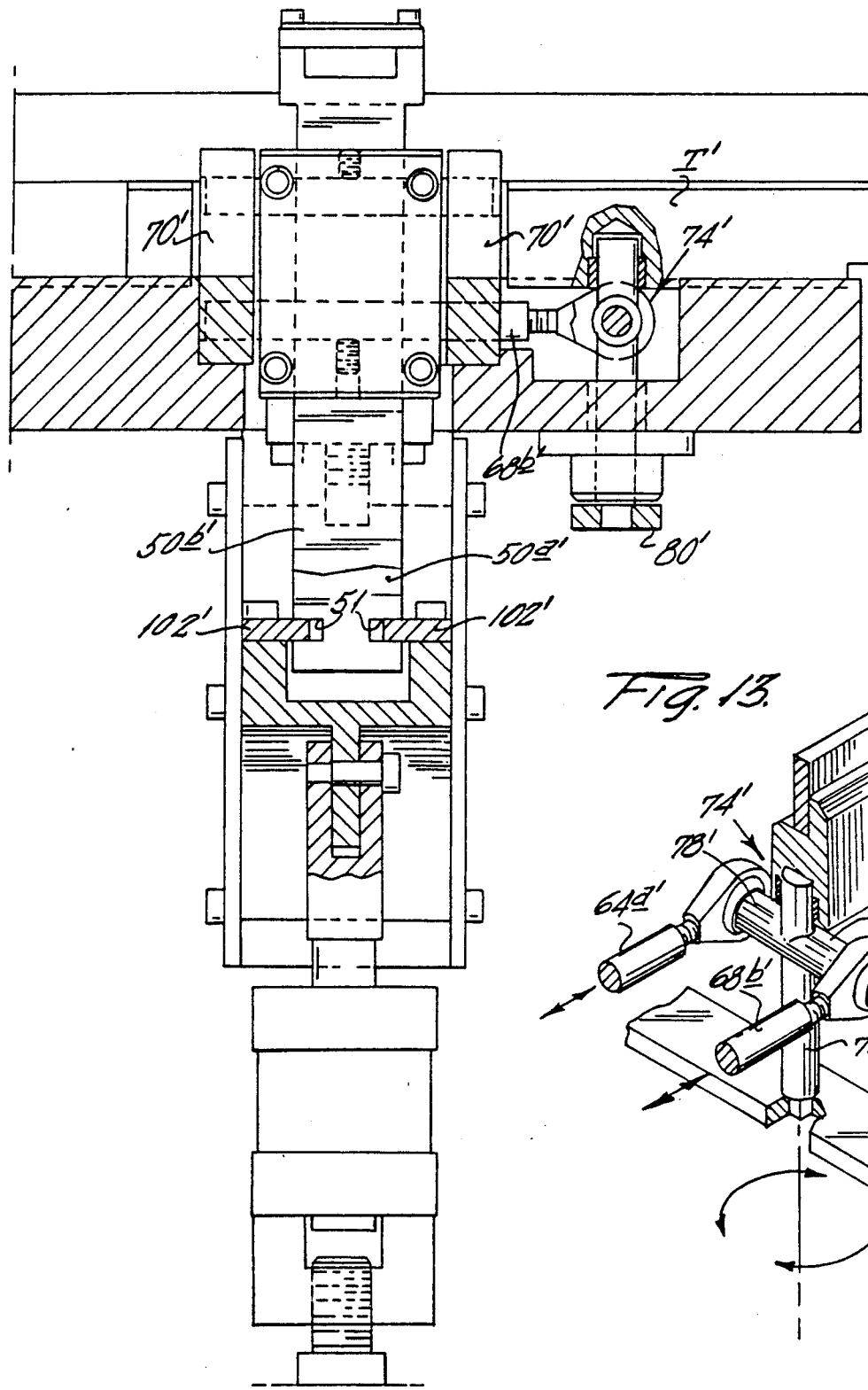
FIG. 12 is a sectional side elevational view taken along line 12—12 of FIG. 8 showing additional details of the pin straightening mechanism and a portion of the means for oscillating the pin straightening heads.
Figure 13:
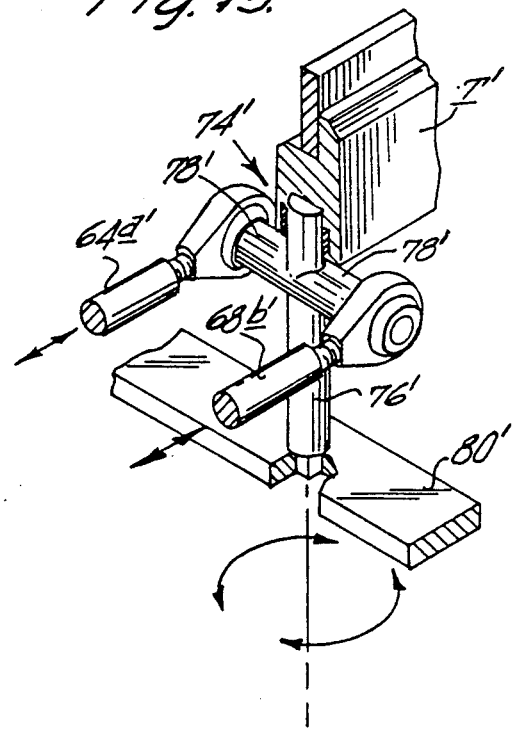
FIG. 13 is a fragmentary perspective view of the yoke assembly, utilized in imparting an oscillatory motion to the straightening heads.

The heads 28a and 28b are preferably oscillated in opposite directions relative to one another through a mechanism best shown in FIGS. 12, 13 and 17 in a direction parallel to or aligned to the trackway T.

Thus each slide 50a, 50b is mounted in two independent slide retaining guide blocks 52a, 52b and each retaining block is mounted on a pair of stub shafts 62a, 64a, 66b, 68b, which in turn are slidably mounted at their outer ends to fixed frame members 70 forming a part of the main housing. The guide blocks 52a, 52b are adjustable relative to the stub shafts 62a, 64a, 66b, 68b and set screws are provided to hold the guide blocks in a fixed position on the stub shafts. The lower stub shafts 64a and 68b are connected to a yoke assembly broadly designated by the numeral 74 (see FIGS. 12, 13 and 15). The straightener heads are connected together for the oscillating movement described at the lower stub shafts 64a and 68b via the yoke assembly 74 which comprises an upstanding vertical shaft member 76 mounting cross shafts 78, 78 connected at their outer ends to universal rotary bearing links threaded to the terminal ends of the stub shafts 64a and 68b. The vertical shaft 76 is rotatably mounted in bearings in the trackway T and baseplate $B_p$ as best illustrated in FIGS. 12 and 13. Thus oscillating movement of the cross shafts 78, 78 imparts back and forth oscillating movement of the straightener heads through the stub shaft 64a and 68b. The vertical shaft 76 is connected at its lower end in a non-rotatably fashion to an elongated actuating link 80. The outer ends of the link 80 abut adjustable pivot limiting assemblies 82a and 82b. (See FIG. 17) Each assembly includes a spring biased positioning head 83a, 83b abutting arcuate cam elements 85a, 85b on the outer terminal ends of the connecting link 80 and a vernier adjustment 84 determines the allowed pivotable movement of the link 80 about an axis through the shaft 16. The positioning head is spring returned to always maintain contact with the cam follower 85a, 85b. A piston-cylinder actuator 90 cycles the link 80.

During what may be termed the initial DIP alignment portion of the lead straightening cycle wherein the DIP devices are floating on the trackway T and the straightening fingers or blades 40 are leafing between the leads of the DIP device, moveable support means is provided to prevent bending or damage to the leads in this phase of the cycle. To this end, a pair of support plates 92a, 92b are pivotally mounted on opposite sides of the trackway at the lead straightening station $S_s$ and are normally spring biased inwardly so that they lie flush against the trackway and wherein the upper faces 92c define support surfaces for the pads of the lead. The support plates 92a, 92b are pivotally mounted at their lower ends to slide blocks 94a and 94b and are nested inside the slide blocks as best illustrated in FIG. 8. The slide blocks 92a, 92b are biased upwardly by pins 96a and 96b of air cylinder 98a and 98b. In this manner, the slide blocks 92a, 92b are normally biased gently upwardly to lightly engage the upper edges of the support blocks against the pads $P_p$ of the DIP device at the straightening station. The support plates are normally spring biased inwardly against the opposing faces of the trackway T and have a relief edge at their lower end to permit outward pivoting movement shown in FIG. 8 when the straightening blades 40 are moved to their operating position shown in full lines in FIG. 9 and 11. FIGS. 10 and 11 show the position of the support plates described above. This type of arrangement is important to provide a firm but yielding support for the pads $P_p$ during the time the separating blades are moving in the gap or breach between adjacent pins of the DIP device and before locking the DIP device in place for the oscillating action for straightening the pins.

Figure 16:
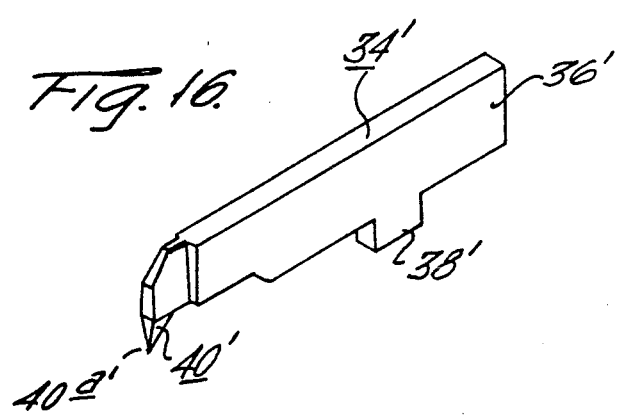
FIG. 16 is a perspective view of one of the DIP lead straightening blades that arranged in series adjacent one another comprise the combs of the straightening heads as shown in FIGS. 14 and 15.
Figure 20:
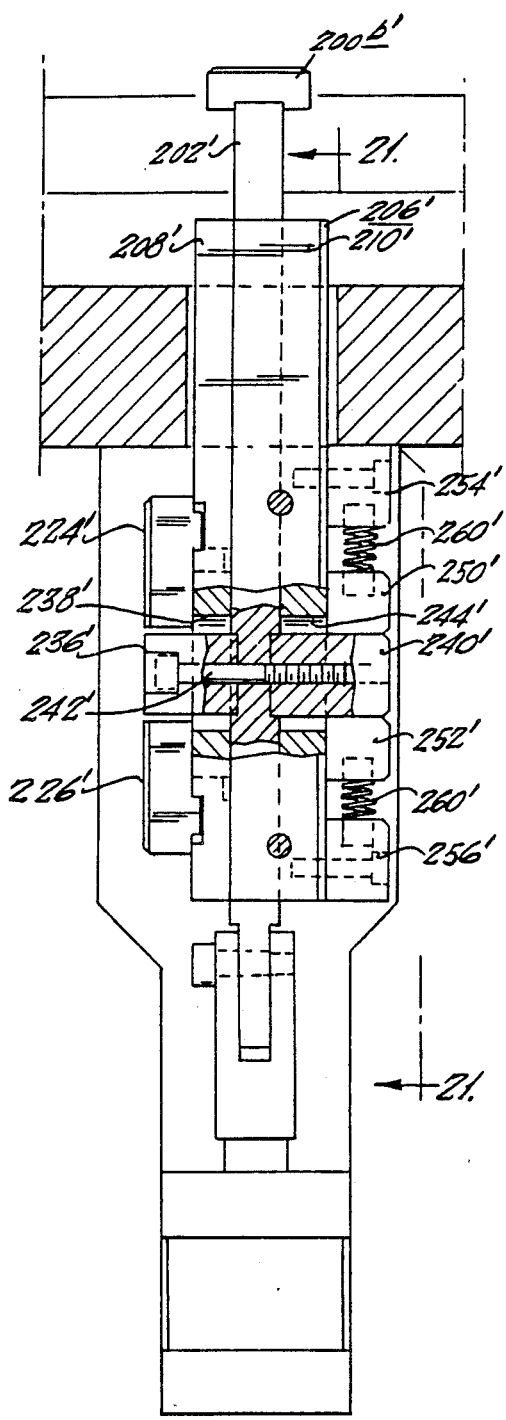
FIG. 20, is a fragmentary sectional side elevational view taken along lines 20—20 of FIG. 18 showing additional details of the coplanarity adjusting station.

The particular configuration of the straightening blades and particularly the shape of the teeth 40a formed on one end of each blade is important in achieving the desired combing and straightening action described above. Thus, the tip 40b of each tooth 40a has a depending pick like shape. The particular geometry of the tip of the blade 40 is best shown in FIG. 16 wherein the pick like shape is generally triangularly shaped. The mid point of the tip 40b is of a greater cross section as at 40c than the tip 40b. By this configuration the mid point of the teeth fill the space between the leads to insure a good straightening action when the heads are oscillated. In other words, the pick like structure of the tooth permits initial entry of the blades to the spaces between the pins without damage and the large mid-section 40c of the blade then fills the gap between adjacent leads so when the heads are actuated, the displacement of the leads or pins P to either side of the vertical plane V—V takes place during the straightening action.

The present apparatus can be easily modified to replace the trackway and the heads can be adjusted outwardly to accommodate a wider trackway. As best shown in FIGS. 8 and 12, the slide guides and guides for the straightening heads are movable outwardly relative to one another to accommodate a larger trackway. It is noted that the lower end of the slides 50a and 50b are mounted by keys 102 which engage in slots 51 having sufficient play to accommodate trackways of various widths. This connection permits the necessary relative displacement of the slides outwardly relative to one another or into and out of the plane of the paper with respect to FIG. 12.

The configuration of the straightening heads 28a and 28b and particularly the mounting of the separating blades 34 provides the advantage that the blades 34 can be easily replaced if necessary to accommodate DIP devices having leads P that are spaced differently and require a different set of blades. In other words, the head assemblies have a universal application to DIP devices irrespective of the gap between adjacent pins. The changeover is simply accomplished by removing the top cap 42 and inserting the blades 34 having the appropriate spacing for a given DIP device. The machine is adaptable from an eight (8) pin to a twenty eight (28) pin DIP device as shown in the drawings.

When the oscillating cycle of the straightening heads is completed, the guide rail assembly $C_R$ clamping the DIP device at the straightening station is retracted as well as the second indexing pin 26 whereby the DIP device moves by gravity to the next adjacent coplanarity station $S_c$.

Consider now the coplanarity station $S_c$, the details of which are best shown in FIGS. 18–21 inclusive.

Figure 21:
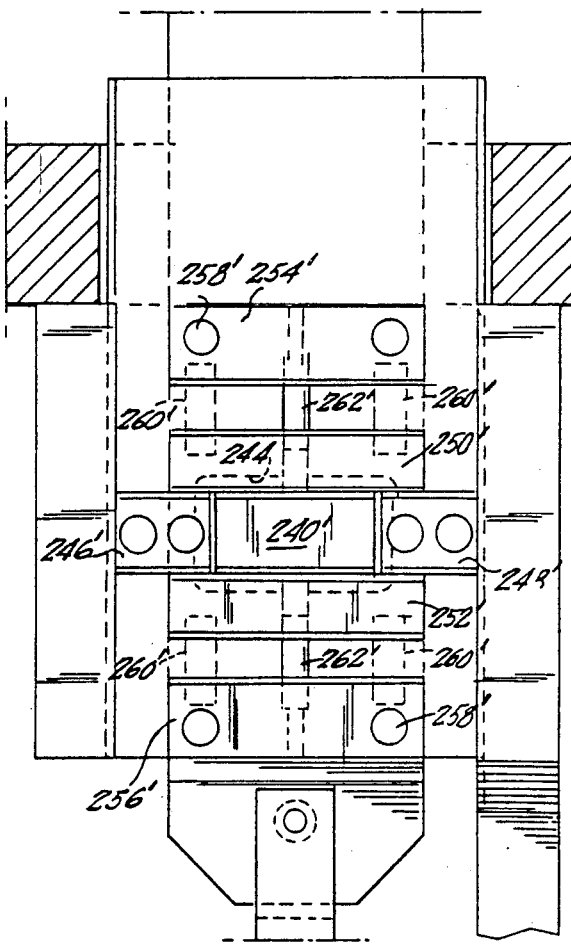
FIG. 21 is a fragmentary sectional rear elevational view taken along lines 21—21 of FIG. 20.

The coplanarity heads 200a and 200b are connected to a common slide 202 which is mounted for reciprocating movement by a piston-cylinder actuator 204 connected to the base plate $B_p$. The slide 202 is confined for sliding movement in the pocket of a slide housing 206 formed by a number of front panel 208 and rear panel 210 in turn connected to the base plate $B_p$ by mounting blocks 212 and 214. A pair of micrometers 216 and 218 are mounted on one sidewall of mounting block 214 and axially aligned and opposed are two adjustable spring biased piston heads 220 and 222 mounted to block 212. Intermediate the micrometers heads 216, 218 and the spring biased piston heads 220, 222 are adjustably mounted limit blocks 224 and 226. Limit block 224 is positioned between micrometer head 216 and spring biased piston head 220 and limit block 226 is positioned between micrometer head 218 and spring biased piston head 222. The limit blocks 224 and 225 are adjustably mounted to the front panel 208 of the fixed housing 206 by way of two diagonally opposed slots 228 and 230 formed in the front panel 208 and secured in a desired position by means of set screws 232 and 234. The slots 228 and 220 form tracks for the blocking 224 and 226 to slide in. The slide 202 has a rectangular striker block 236 fixedly mounted to its front face by means of screws. The strike block 236 projects through a rectangular aperture 238 spaced midway between the diagonal slots 228, 230. The slide then is free to move vertically between the lower surface of limit block 224 and the upper surface of limit block 225. The vertical placement of the limit blocks 224 and 226 determines the upward and downward travel of the slide 202, and the coplanarity heads 200a and 200b. When a 2-way cylinder 201 is deactivated, the slide 202 and heads 200a and 200b also assume a rest or normal position that places the block 236 at the midpoint of the window 238 irrespective of the positioning of limit blocks 224, and 226. The rest or normal position of the slide 202 and heads 200a and 200b is accomplished by the following means with a reference to FIGS. 20 and 21. The slide 202 has fixedly secured to its rear face a second rectangle positioning block 240. The striker block 236 and the positioning block 240 are both secured to the slide 202 with the same mounting screws 242. The positioning block 240 projects through a rectangular aperture 244 in the rear panel 210 of the slide housing 206. As shown in FIG. 21 Fixed rectangular edge blocks 246 and 248. Blocks 246 and 248 are mounted on the left and right hand side of aperture 244 and centrally located with respect to the aperture 244 to the slide housing 206,and positioning block 240 have the same cross sectional thickness, the upper and lower faces forming a common plane. Spring biased bearing blocks 250 and 252 span the upper and lower faces of the edge blocks 246 and 248 and centrally position, the centering block 240 between them when no force is applied thereby positioning the slide 202 and the coplanarity heads 200a and 200b in a desired rest position. The bearing blocks 250 and 252 are spring biased toward each other in the following manner. Rectangular anchor blocks 254 and 256 are secured to the rear panel 210 of the slide housing 206 by means of mounting screws 258. Between each anchor block and bearing block there are positioned two springs 260. Bearing block guide pins 262 are centrally positioned between anchor blocks 254 and 256 and bearing blocks to both guide and retain the spring biased bearing blocks 250 and 252.

Having now described the specific structural details and actuating mechanisms for the coplanarity heads, consider now the action of the heads on a DIP device when it arrives at the coplanarity station $S_C$. A DIP device advances along the trackway T by gravity and is brought to rest at the coplanarity station by engaging a second indexing pin 27. The coplanarity heads at this time are in a rest position (See FIG. 19). The photo detectors Pe sense the presence of a DIP device at the coplanarity station and effect actuation of the clamping guide rail assembly $C_R$ to securely clamp the DIP device to the trackway T for the cycling of the coplanarity heads in the manner described above. The coplanarity heads as described previously, first engage all the pads and bend them about the shoulder point connection to one side of the desired horizontal plane H—H; first downwardly of the plane H—H to a lower limit position. The limit blocks just described, which are selectively adjustable determine the lower limit position of the coplanarity heads. This mechanism provides a simple and precise means for adjusting this lower limit position. The coplanarity heads are then cycled upwardly to a position where the lower faces of the pads $P_P$ lie in the plane H—H. The piston cylinder actuator then is deactivated whereby the spring 260 returns the coplanarity heads to the neutral or home position shown in FIG. 19. The upper and lower limit positions are simple to adjust by simply loosening the screws to 232 and 234. The fine tuning adjustment can then be made through the verniers 216 and 218, the blocks of course being held firm during adjusting movement by the spring biased pistons 220 and 222. After a new adjustment has been accomplished which adjusts the gap between the striker plate and the blocks 224 and 226, the screws 232 and 234 are simply re-tightened.

Figure 22:
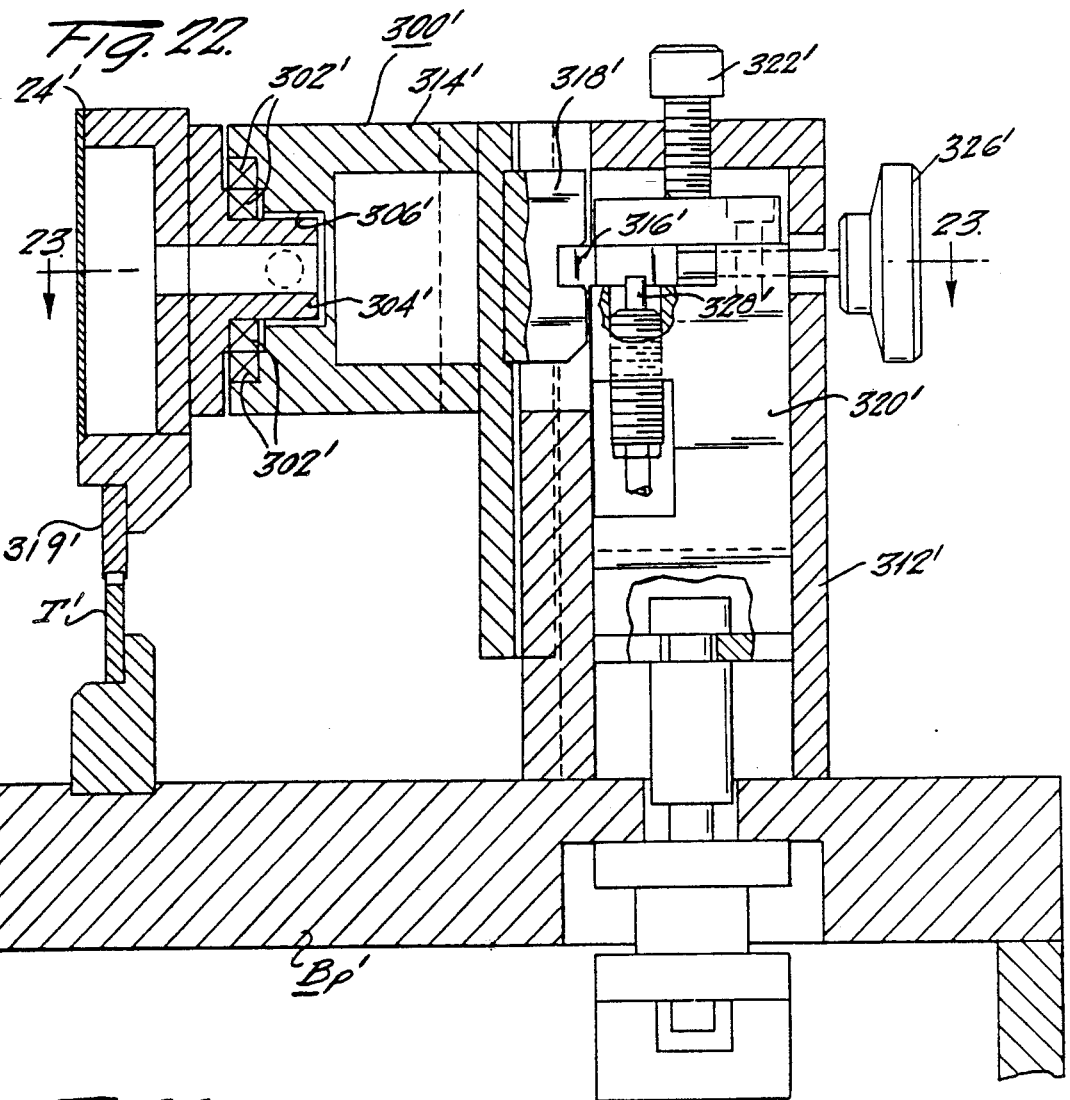
FIG. 22 is an enlarged fragmentary elevational view taken on the lines 22—22 of FIG. 4 showing details of the adjustable support and actuating means for the clamping and guide rail assembly.
Figure 23:
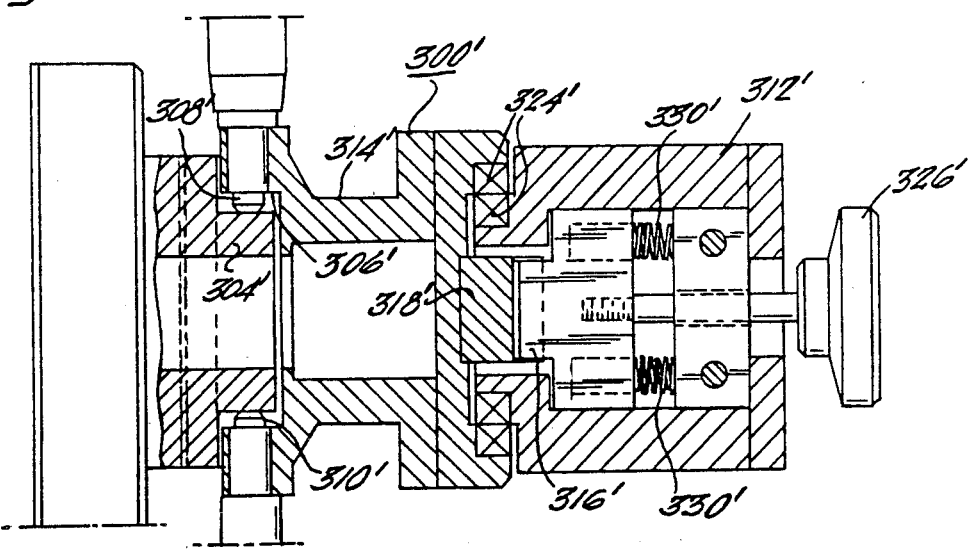
FIG. 23 is a sectional plan view taken on the lines 23—23 of FIG. 22 showing additional details of the clamping an guide rail assembly.

Another feature of the present invention is shown in FIGS. 22 and 23. The mechanism illustrated here is useful in facilitating disassembly of the clamping and guide rail assembly $C_R$ in the event of a power failure.

This mechanism is used for initially setting up the machine for a given DIP device and additionally permits access to the machine in the event of a power failure or malfunction such as jamming of the DI device. Thus this mechanism is important for initial set up and trouble shooting of the apparatus.

The clamping and guide rail assembly is mounted in a cantilevered support frame 300 on the base of the main frame $B_p$. The clamping and guide $C_R$ rail assembly is adapted for adjusting longitudinal movement relative to the trackway T to permit, for example, adjustment of the escapement $S_e$ indexing pin, at the straightening station, (see FIG. 13) and to this end is mounted in linear bearings 302. The guide rail assembly $C_R$ has a rearward extension 304 which is mounted in a complementary opening 306 in the cantilevered support 300 to accommodate vernier adjustment means of the type shown in FIG. 23. This adjustment comprises a vernier mounted piston micrometer head 308 which bears against the block 304. The adjustment is made against a spring bias backing support 310.

The cantilevered support 300 includes an upstanding fixed support element 312 mounted on the base. The cross arm 314 of the cantilever support which carries the guide and clamping rail is connected to an actuating system via a spring biased tang 316 engaging in a slotted block 318 mounted to the cross arm 314. The block 318 is connected to a carriage 320 by means of tang 316. The gap between the upper surface of trackway T and the underface of the guide rail 319 of assembly $C_R$ is selectively adjustable and controlled by a screw member 322 which engages the top of the carriage 320 and back of piston-cylinder 325 to limit the throw of the piston cylinder actuator. The carriage 320 moves vertically in support element 312 and cross arm 314 is guided in linear bearings 324. Adjustment screw 323 engaging piston-cylinder actuator 325 provides means for controlling relative spacing between guide rail 319 and upper surface of trackway T (See FIG. 22).

With reference to FIG. 22, it can be seen that in normal vertical adjusting movement of the clamping and guide rail assembly $C_R$ to clamp and release the DIP devices in the various manners described above, the cross head 314, block 318 are keyed integrally via tang 316 to the piston cylinder actuator 320. The actuator as best shown in FIG. 23 is mounted for this vertical adjusting movement in linear bearings 324. Further in normal operation, the air cylinder rod 328 is engaged and maintains the parts in the interlocked relationship described. In the event of a malfunction or loss of air pressure, air cylinder rod 328 releases downwardly and thus tang 316 can be withdrawn from its seat in block 318. Accordingly, piston-cylinder actuator 320 may be retracted manually by a knob actuator 326 thereby releasing block 318 and permitting manual disassembly of the cross arm 314 and its associated clamping and guide rail assembly $C_R$. This permits the trackway and the associated part of the cantilevered assembly to be removed vertically and upwardly and away from the trackway and apparatus. In normal operation, air cylinder rod 328 prevents displacement of the tang 316. In the event of power failure, this pin 328 automatically drops to a release position permitting the manual disassembly described above. Note that tang or block 316 is normally spring biased to the locking position by spring 330. (See FIG. 21)

The coplanarity system of the present invention works the leads in such a manner to insure maintenance of the desired so called lead stand off height necessary for proper installation. This height designated $H_L$ in FIG. 2b is the distance between the lower face of the body portion B and the plane H—H.

What is claimed is:

1. Apparatus for aligning the leads of electronic devices having a body portion and plurality of leads extending from the body portion having pads at the free terminal ends comprising:
    means for positioning an electronic device at a lead straightening station including a trackway,
    at least one lead straightening head comprised of a plurality of fingers engageable between the leads of the electronic device;
    means for actuating the heads relative to the electronic device through a straightening cycle; and
    pivotally mounted support plates disposed on opposite sides of said trackway at the lead straightening station engageable by the pads of the leads during the straightening cycle to provide a firm but yielding support for the pads, said support plates pivotable outwardly by fingers of the straightening heads during the straightening cycle.

2. An apparatus as claimed in claim 1 including an escapement station located on the trackway upstream of the straightening station adjacent the lead straightening station comprising a series of escapement pins mounted in an upper guide rail housing overlying the trackways for reciprocating movement therein, said lead pin constituting an index pin to retain the line of electronic devices at the escapement station, said other pins constituting clamping pins and being selectively actuated in unison with the stop pin depending on the size of the electronic device being processed whereby said index pin only retracts to release an electronic device when one of said other clamping pins is in an operative clamping mode.

3. An apparatus as claimed in claim 1 including an indexing pin to locate an electronic device in a predetermined position at the straightening station permitting leafing interengagement fingers of the straightening heads during the initial phase of the straightening cycle.

4. An apparatus as claimed in claim 1 wherein the each of said straightening heads is of similar construction and comprises a U-shaped block having an elongated key slot in its base and a plurality of elongated straightening blades having an elongated body and a depending lug which keys in a slot to align the blades so tat the teeth are spaced and generally aligned to engage in the spaces between the leads of an electronic device.

5. An apparatus as claimed in claim 1 wherein said means for actuating the straightening heads includes elongated slides (50A, 50B) slidably engaged in slide retaining blocks (52A, 52B), said slides being connected to their ends at a cross head (54), which in turn is connected to a piston cylinder actuator (56) whereby cycling of the piston-cylinder actuator effects reciprocating movement of the cross head (54), the slides (52A) and (52B) and the straightening heads (28A and 28B).

6. An apparatus as claimed in claim 5 wherein said retaining guide blocks are mounted on a pair of stub shafts which in turn are slidably mounted at their outer ends to fixed frame members, said guide blocks being adjustable relative to the stub shafts, the stub shafts being connected to a yoke assembly which connects the straightening heads together, whereby oscillating movement of the cross shafts imparts a back and forth oscillating movement of the straightening heads through the stub shafts (64A) and (68B).

7. An apparatus as claimed in claim 5 wherein said support plates are pivotably mounted at their lower ends to slide blocks by piston cylinder actuators to normally biased upwardly to lightly engage the upper edges of the support blocks against the pads of the electronic components at the straightening station.

8. An apparatus as claimed in claim 1 including means for oscillating the heads during the straightening cycle.

9. An apparatus as claimed in claim 1 including biasing means for normally urging the support plates against the opposing faces of the trackway and including a relief edge at their lower end to permit outward pivoting movement when the straightening heads are cycled.

10. An apparatus as claimed in claim 1 wherein the fingers include straightening teeth having a depending pick-like tip of triangular shape wherein the mid point of the tip is of a greater cross section than the tip so that the mid point of the teeth fill the space between the leads to ensure a good straightening action when the straightening heads are cycled.

11. An apparatus as claimed in claim 1 wherein said guide rail assembly is mounted in a cantilevered support frame having a cross arm (314) which carries the guide rail connected to an actuating means via a spring bias tang engaging in a slotted block (318) mounted to the cross arm (314), whereby the gap between the upper surface of the trackway and the under surface of the guide rail may be selectively varied.

12. In a system for aligning the leads of electronic components having a body portion and a plurality of leads connected to the body portion at a shoulder junction and terminating in pads at the free terminal ends so that the pads are disposed in a predetermined common plane comprising;
   means for guiding and clamping the body portion in a fixed position; and
   means for engaging the pads and pivoting the leads about the shoulder to both sides of said common plane whereby the spring back returns all leads to said common plane thereby to align the pads in said predetermined common plane.

13. An apparatus as claimed in claim 12 wherein said means for cycling said copolanarity jaws comprises a slide (202) mounted for sliding movement in a pocket of slide housing (206) in turn connected to base plate by mounting blocks (212) and (214), adjustable means including adjustable spring bias piston heads.

14. An apparatus as claimed in claim 13 including adjustable means for determining the limit positions of the coplanarity heads.

15. An apparatus as claimed in claim 12 wherein the means for cycling the coplanarity heads includes a piston cylinder actuator and spring biasing means for normally biasing the coplanarity heads to a neutral or home position.

16. The apparatus as claimed in claim 12 wherein the means for positioning a single electronic device at the lead straightening station comprises a series of pins spaced along the trackway including a first indexing pin and a series of escapement pins up stream of the straightening station which retain a line of electronic devices at the escapement station and release electronic devices one at a time to the straightening station.

17. Apparatus as claimed in claim 12 wherein the means for clamping the electronic devices in a selected location on the trackway comprises a clamping guide rail assembly overlying the trackway and having actuator means for reciprocating the guide rail in an up and down fashion from a position overlying and slightly spaced above the trackway so that the electronic devices are free to move by gravity along the trackway and a lower position to clamp a electronic device in place.

18. Apparatus as claimed in claim 17 wherein the guide rail actuator includes means for manual disassembly of the guide rail to access the trackway.

19. A method for aligning leads of electronic devices by means of straightening heads having a plurality of fingers, the electronic devices having a body portion and a plurality of leads extending from the body portion terminating in pads extending angularly to the leads consisting of the steps of:
   engaging the tips of fingers of lead straightening heads between the leads of the electronic device;
   supporting the pads on a support surface during a lead straightening cycle;
   clamping the electronic device in the support surface; and
   oscillating the straightening heads to displace the leads to opposite sides of a predetermined first plane extending transverse to the body portion and generally parallel to the leads to overcome spring back and align all the leads generally parallel to said first plane and to one another.

20. A method for aligning leads of electronic devices by means of straightening heads having a plurality of fingers, the electronics devices having a body portion and a plurality of leads extending from the body portion terminating in pads extending angularly to the leads consisting of the steps of:
   positioning the fingers of the straightening heads between the leads at the juncture of the leads and body portion and actuating the heads to produce a combining action of the leads by the fingers;
   supporting the pads on a pivotal support surface extending generally transversely to the direction of combing; and
   pivoting the support surface by the fingers to provide a firm but yielding support for the pads.

21. A method for aligning the leads of electronic components having a body portion and a plurality of leads connected to the body portion at a shoulder junction and terminating in pads at the free terminal ends of the leads so that the pads are disposed in a predetermined common plane consisting the steps of;
   clamping the body portion in a fixed position; and
   engaging the pads and pivoting the leads about the shoulder to both sides of said common plane whereby the spring back returns all leads to said common plane thereby to align the pads in said predetermined common plane.

* * * * *